United States Patent
Belleville et al.

(10) Patent No.: US 10,349,840 B2
(45) Date of Patent: Jul. 16, 2019

(54) METHOD FOR PRESSURE GUIDEWIRE EQUALIZATION

(71) Applicant: OPSENS INC., Quebec (CA)

(72) Inventors: Claude Belleville, Québec City (CA); André Lachance, Lévis (CA); Étienne Côté, Lévis (CA)

(73) Assignee: Opsens Inc., Montreal (CA)

( * ) Notice: Subject to any disclaimer, the term of this patent is extended or adjusted under 35 U.S.C. 154(b) by 810 days.

(21) Appl. No.: 14/850,606

(22) Filed: Sep. 10, 2015

(65) Prior Publication Data

US 2017/0071486 A1    Mar. 16, 2017

(51) Int. Cl.
| | | |
|---|---|---|
| *A61B 5/0215* | (2006.01) | |
| *A61B 5/00* | (2006.01) | |
| *A61B 5/02* | (2006.01) | |
| *A61B 5/026* | (2006.01) | |
| *A61B 5/029* | (2006.01) | |

(52) U.S. Cl.
CPC ...... *A61B 5/02156* (2013.01); *A61B 5/02007* (2013.01); *A61B 5/6851* (2013.01); *A61B 5/6852* (2013.01); *A61B 5/7278* (2013.01); *A61B 5/026* (2013.01); *A61B 5/029* (2013.01); *A61B 2560/0223* (2013.01); *A61B 2560/0247* (2013.01); *A61B 2562/0247* (2013.01); *A61B 2562/168* (2013.01)

(58) Field of Classification Search
None
See application file for complete search history.

(56) References Cited

U.S. PATENT DOCUMENTS

| | | | | |
|---|---|---|---|---|
| 5,746,698 A | * | 5/1998 | Bos | A61B 5/022 600/485 |
| 6,767,327 B1 | * | 7/2004 | Corl | A61B 5/0215 600/486 |
| 2002/0099298 A1 | * | 7/2002 | Yokozeki | A61B 5/02116 600/494 |
| 2004/0097813 A1 | * | 5/2004 | Williams | A61B 1/00082 600/485 |
| 2004/0167415 A1 | * | 8/2004 | Gelfand | A61B 17/12036 600/500 |
| 2010/0241008 A1 | * | 9/2010 | Belleville | A61B 5/0215 600/478 |
| 2011/0295146 A1 | * | 12/2011 | Gefen | A61B 1/00082 600/561 |
| 2012/0172732 A1 | * | 7/2012 | Meyer, Jr. | A61B 5/6851 600/487 |

(Continued)

*Primary Examiner* — Patricia Mallari
*Assistant Examiner* — Jairo H Portillo
(74) *Attorney, Agent, or Firm* — Benoit & Cote, Inc.; C. Marc Benoit

(57) ABSTRACT

The present document describes a system for equalizing the pressure of a pressure guidewire against the pressure of an aortic pressure device: the system comprising two methods of equalizing the pressure against each other, one method that involves a gain adjustment and another method that involves the addition of an offset; the method further comprising a method for detecting which method should be applied to the situation, the detecting methods including: the contribution of the operator; an algorithm detecting the first equalization from subsequent post procedure equalizations, the algorithm including various factors such as incrementing the equalization requests, measuring the elapsed time and others.

20 Claims, 9 Drawing Sheets

(56) References Cited

U.S. PATENT DOCUMENTS

| | | | |
|---|---|---|---|
| 2013/0345574 A1* | 12/2013 | Davies | A61B 5/02007 600/486 |
| 2014/0081244 A1* | 3/2014 | Voeller | A61M 25/01 604/528 |
| 2014/0276139 A1* | 9/2014 | Burkett | A61B 5/02156 600/486 |
| 2015/0141854 A1* | 5/2015 | Eberle | A61B 5/02154 600/488 |

* cited by examiner

METHOD FOR PRESSURE GUIDEWIRE EQUALIZATION

BACKGROUND (a) Field

The subject matter disclosed generally relates to the field of methods and devices used for making measurements in the medical field. More specifically, it relates to methods and devices for the accurate measurement of fractional flow reserve.

(b) Background of the Invention

Pressure guidewires are 0.014" guidewire comprising an embedded pressure transducer devoted to measure intracoronary pressure. More specifically, these guidewires are used to measure the pressure distal to a lesion. By calculating the ratio between the measured pressure distal to the lesion and some point more proximal, most commonly in the ascending aorta or nearby the coronary oestium, the fractional flow reserve (FFR) is obtained. The FFR is now commonly used to assess the severity stenosis and thereby informs the physician as to the most appropriate treatment strategy. Recently there has been greater clinical acceptance of the importance of measuring translesional pressure and calculating FFR prior to deciding whether to place a stent. As detailed in Fearon et al. "Rationale and design of the fractional flow reserve versus angiography for multi-vessel evaluation (FAME) study" American Heart Journal (2007) vol. 154 (4) pp. 632-636, which is hereby incorporated by reference, FFR guided PCI therapy leads to better outcome than angiography guided PCI therapy, whereas stenosis with an FFR greater than 0.80 are not stented, while stenosis with an FFR lower or equal to 0.80 are stented.

Although there exists a gray zone with FFR measurements between 0.75 and 0.80 where other factors should be considered for the treatment strategy, the decision to stent or not is strongly influenced by the FFR value, where an error greater than 0.02 is considered as clinically relevant. In order to get an accurate FFR measurement, it is critical to have accurate distal and proximal pressure measurements. A variety of pitfalls exist, such as the positioning of the guide catheter and the height adjustment of the external aortic pressure transducer. However, a careful operator can easily eliminate those factors of error and routinely obtain accurate FFR measurements.

Accurate pressure measurements are obtained by equalizing the pressure guidewire with the aortic pressure. The method used by the systems available on the market involves bringing the pressure guidewire at the site of the aortic pressure, and adding an offset to the pressure guidewire such that both systems display the same level of pressure. Of importance here is the fact that this equalization follows the zeroing of both aortic and distal pressure sensors and hence, there shouldn't be any offset between the pressure sensors, but there should rather be a difference in their respective gain, or the sensitivity of the pressure guidewire (distal pressure sensor) is different from the sensitivity of the aortic pressure transducer (external transducer). The equalization of two pressure sensors, for which pressure zeroing was performed adequately, by way of adding an offset may lead to an error that can be clinically significant.

On the other hand, there are situations where equalizing the pressure by way of adjusting the gain may also lead to clinically significant error. Most of today's pressure guidewires are based on the use of a piezo-electric sensor embedded within the distal end of the guidewire. While from the above it may sound better to equalize those sensors by way of adjusting the gain, it may also lead to very significant error when equalizing a pressure guidewire for which the pressure error results from the re-connection of the guidewire to the interface cable, e.g., after using the pressure guidewire for the delivery of a stent. It is indeed known to those in the art that re-connecting such an electrical guidewire may lead to a pressure error caused by a change in the electrical contacts which is thereby associated to an offset rather than a difference in the gain.

There is therefore a need for a method for equalizing the pressure of a pressure device with the pressure of another pressure transducer in such a way that they both accurately measure a same pressure throughout the duration of a procedure.

SUMMARY

There is described herein a method for equalizing the pressure as measured by a pressure guidewire against the aortic pressure measured by a fluid filled pressure transducer in view of performing physiological pressure measurements for diagnostic purposes.

According to an aspect of the invention, there is provided a method for equalizing one of a pressure of a distal intravascular pressure device (a distal pressure) and a pressure of an aortic pressure device (an aortic pressure). The method comprises: measuring an initial aortic pressure (Pa1) at a site of aortic pressure using the aortic pressure device and measuring an initial distal pressure (Pd1) at the site of aortic pressure using the distal intravascular pressure device; calculating a gain factor (K) by dividing the initial aortic pressure (Pa1) by the initial distal pressure (Pd1); measuring the aortic pressure (Pa') and the distal pressure (Pd') at a site that is distal to the site of the aortic pressure; and gain-equalizing one of: the measured distal pressure by multiplying Pd' by the gain factor (K) thereby producing a gain-equalized distal pressure ($Pd_{eq}$); and the measured aortic pressure by dividing Pa' by the gain factor (K), thereby producing a gain-equalized distal pressure ($Pa_{eq}$).

According to an embodiment, gain-equalizing comprises gain-equalizing the measured distal pressure, and there is further provided averaging the distal pressure, either before or after the gain-equalizing, thereby generating an average gain-equalized distal pressure ([Pd]); averaging the aortic pressure, thereby generating an average aortic pressure ([Pa]); and calculating fractional flow reserve (FFR) by calculating the minimum value of ratio [Pd]/[Pa].

According to an embodiment, the averaging is performed over one of: a given number of cardiac cycles; and a given time period.

According to an embodiment, there is further provided performing an offset equalization of the gain-equalized distal pressure: verifying that the gain factor (K) has been used for the gain equalizing; measuring an aortic pressure (Pa2) using the aortic pressure device and measuring a distal pressure (Pd2) at the site of aortic pressure using the distal intravascular pressure device; calculating an offset value (A) by subtracting the gain-equalized distal pressure from the aortic pressure (Pa2); and offset-equalizing by calculating a gain-and offset-equalized distal pressure (Pdoffset) by adding the offset value (A) to the gain-equalized distal pressure (Pdeq). According to an embodiment, there is further provided averaging the distal pressure, either before or after the gain-equalizing, thereby generating an average gain-equalized distal pressure ([Pd]); averaging the aortic pressure, thereby generating an average aortic pressure ([Pa]); and calculating fractional flow reserve (FFR) by calculating the minimum value of ratio [Pd]/[Pa].

According to an embodiment, there is further provided determining whether the offset-equalizing is required, the determining comprising: verifying at least one of a set of criteria, the set of criteria comprising: an existence of a bubble on a surface of one or both of the distal intravascular pressure device and the aortic pressure device; a manipulation of the distal intravascular pressure device during more than 2 minutes; and a recording of data for a first FFR measurement.

According to an embodiment, verifying that the distal pressure is gain-equalized comprises verifying that a recording has been performed at least once by a monitoring device.

According to an embodiment, there is further provided determining whether another gain-equalizing is required after performing a first gain-equalizing.

According to an embodiment, determining whether another gain-equalizing is required comprises measuring a period after the first gain-equalizing and, when the period is less than a given period, performing once more the calculating a gain factor (K), the measuring a distal pressure (Pd') and the gain-equalizing the measured distal pressure (Pd').

According to an embodiment, the given period is between 5 seconds and 2 minutes.

According to an embodiment, the measuring a distal pressure (Pd') at a site that is distal to the site of aortic pressure comprises measuring a distal pressure (Pd') at a site that is distal to an intravascular lesion using the distal intravascular pressure device.

According to an embodiment, gain-equalizing comprises gain-equalizing the measured aortic pressure, further comprising averaging the aortic pressure, either before or after the gain-equalizing, thereby generating an average gain-equalized aortic pressure ([Pa]); averaging the distal pressure, thereby generating an average distal pressure ([Pd]); and calculating fractional flow reserve (FFR) by calculating the minimum value of ratio [Pd]/[Pa].

According to an embodiment, there is further provided performing an offset equalization of the gain-equalized aortic pressure: verifying that the gain factor (K) has been used for the gain-equalizing; measuring an aortic pressure (Pa2) using the aortic pressure device and measuring a distal pressure (Pd2) at the site of aortic pressure using the distal intravascular pressure device; calculating an offset value (A') by subtracting the gain-equalized aortic pressure from the distal pressure (Pa2); and offset-equalizing by calculating a gain-and offset-equalized aortic pressure ($Pa_{offset}$) by adding the offset value (A') to the gain-equalized aortic pressure (Paeq).

According to an embodiment, there is further provided averaging the aortic pressure, either before or after the gain-equalizing, thereby generating an average gain-equalized aortic pressure ([Pa]); averaging the distal pressure, thereby generating an average distal pressure ([Pd]); and calculating fractional flow reserve (FFR) by calculating the minimum value of ratio [Pd]/[Pa].

According to another aspect of the invention, there is provided a method for equalizing a pressure of one of a distal intravascular pressure device and an aortic pressure device against another one thereof, the method comprising: determining whether one of: gain-equalizing the pressure was previously performed; and gain-equalizing the pressure must be performed; and based on the determining, equalizing the pressure by performing one of: adjusting a gain of the pressure, if the gain-equalizing must be performed; and adding and offset to the pressure, if the gain-equalizing was previously performed.

According to another aspect of the invention, there is provided a system used in performing of fractional flow reserve (FFR) measurements in which takes place an equalizing of a distal pressure against an aortic pressure, the system comprising: a distal intravascular pressure device for measuring distal pressure; an aortic pressure device for measuring aortic pressure; a monitoring device comprising a computer adapted to execute instructions comprising: measuring an initial aortic pressure (Pa1) at a site of aortic pressure using the aortic pressure device and measuring an initial distal pressure (Pd1) at the site of aortic pressure using the distal intravascular pressure device; calculating a gain factor (K) based on the initial aortic pressure (Pa1) and the initial distal pressure (Pd1); measuring a distal pressure (Pd') at a site that is distal to the site of aortic pressure; and gain-equalizing the measured distal pressure by multiplying Pd' by the gain factor (K) thereby producing an equalized distal pressure (Pdeq).

According to an embodiment, the computer further executes instructions comprising: averaging the distal pressure, either before or after the gain-equalizing, thereby generating an average gain-equalized distal pressure ([Pd]); averaging the aortic pressure, thereby generating an average aortic pressure ([Pa]); and calculating fractional flow reserve (FFR) by calculating the minimum value of ratio [Pd]/[Pa].

According to an embodiment, the computer further executes instructions comprising: after the gain-equalizing, measuring an aortic pressure (Pa2) using the aortic pressure device and measuring a post procedure distal pressure (Pd2) at the site of aortic pressure using the distal intravascular pressure device; calculating an offset value (A) by subtracting a gain-equalized distal pressure from the aortic pressure (Pa2); and calculating a gain-and offset-equalized distal pressure (Pdoffset) by adding the offset value (A) to the gain-equalized distal pressure (Pdeq).

According to an embodiment, the distal intravascular pressure device comprises a pressure guidewire.

According to an embodiment, the aortic pressure device comprises a catheter for sliding onto the pressure guidewire.

BRIEF DESCRIPTION OF THE DRAWINGS

Further features and advantages of the present disclosure will become apparent from the following detailed description, taken in combination with the appended drawings, in which.

It will be noted that throughout the appended drawings, like features are identified by like reference numerals.

DETAILED DESCRIPTION

An intravascular pressure device can be one of a guidewire comprising an embedded pressure sensor, most commonly referred as a pressure guidewire, a catheter capable of sliding over a guidewire and comprising an embedded pressure sensor, or any other similar devices used to deliver a pressure sensor within the vascular system. Although coronary pressure guidewires are typically of 0.014", other dimensional characteristics are possible, especially when considering the use of such a pressure guidewire for peripheral uses. While we will be using the expression "pressure guidewire" in the description herein, it is understood we are referring more generally to an intravascular pressure device.

It is also understood that although generally referring herein to the aortic pressure as the pressure against which the pressure guidewire is equalized, the aortic pressure includes in the description herein any site against which to equalize.

The distal pressure always refers herein to the pressure measured by a pressure guidewire, i.e., a pressure distal to a lesion (Pd), while the proximal pressure always refers to the aortic pressure, i.e., the pressure proximal to the lesion (Pa).

Figure 1:
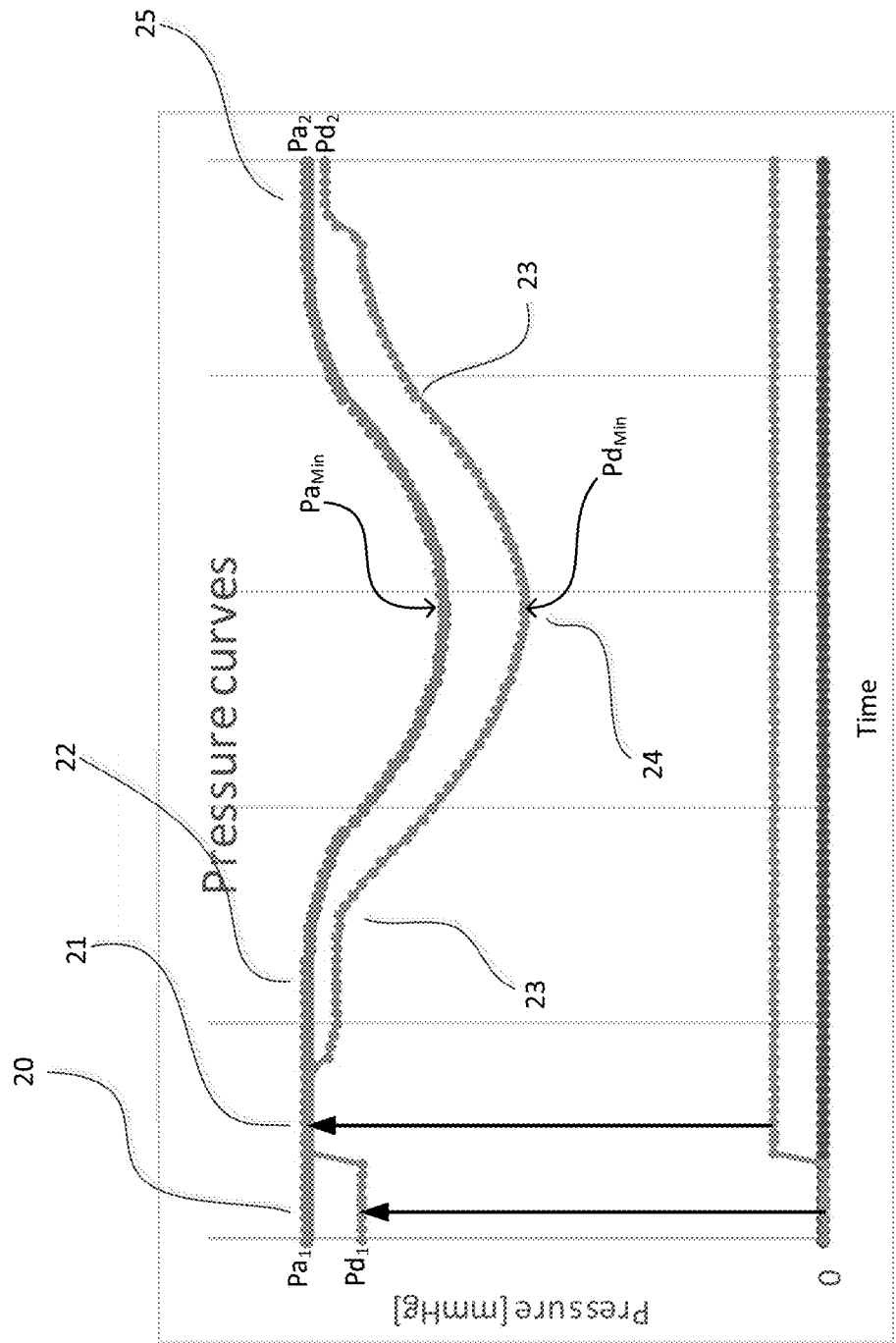
FIG. 1 is a graph which illustrates the pressure measurements during a typical sequence of events for an FFR procedure.

A typical sequence of event for an FFR procedure is shown using FIG. 1 where the pressure measurement (y axis) taken using a monitoring device is graphed as a function of relative time elapsed during a FFR procedure (x axis). Both the aortic pressure transducer and the distal pressure are first zeroed. Zeroing is performed by having the aortic pressure valve open to atmospheric pressure, hence disconnected from blood pressure, and having the pressure guidewire resting outside the blood vessel or the guiding catheter, and exposed to atmospheric pressure. The pressure guidewire is thereafter brought at the distal end of the guiding catheter, where the same aortic pressure is applied to both sensors. Although they should display the same pressure, there is typically a difference between the aortic pressure $Pa_1$ and the distal pressure $Pd_1$ as illustrated in region 20. While both sensors are exposed to the same pressure, the distal pressure is equalized by way of adding an offset as shown in region 21. From there, the pressure guidewire is advanced across the lesion of interest, where a pressure drop representative of the severity of the stenosis occurs in region 22. Maximal hyperemia is thereafter simulated by injecting a vasodilator, typically adenosine. Injection of adenosine in region 23 is followed by a decrease of the microvasculature resistance, therefore inducing an increase of the blood flow and a further decrease of the distal pressure, again representative of the severity of the lesion. The injection of adenosine is often accompanied by a drop of the aortic pressure. Upon injection of a vasodilator, Pd/Pa in region 24 reaches a minimum, which is the point of interest as it corresponds to the FFR value. The effect of adenosine lasts for a few seconds after which the vasodilatation ceases and aortic and distal blood pressure increase in region 26. Existing pressure guidewires may encounter drift issue, which translates into a difference between the post-procedure aortic pressure $Pa_2$ and post-procedure distal pressure $Pd_2$ shown in region 25. Drifts can take place as a result of a variety of phenomena, but it mostly manifests as a shift of the whole pressure signal or said otherwise, the drift causes the pressure to offset. The procedure can thereafter continue after the both distal and aortic pressures are equalized again.

Figure 2:
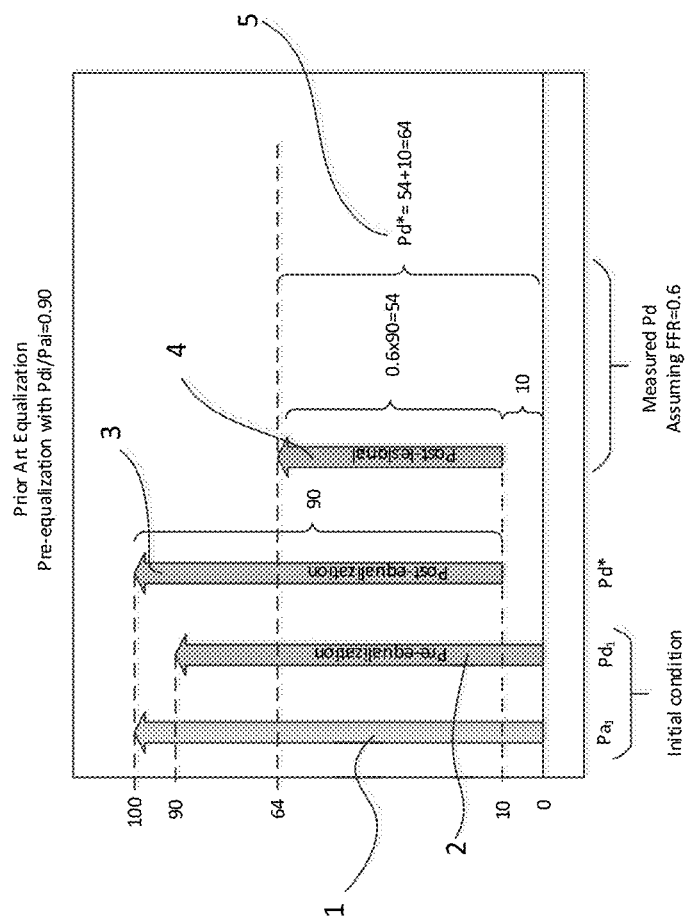
FIG. 2 is a chart which illustrates the known method of equalizing a pressure guidewire against the aortic pressure transducer.

Assuming both sensors are zeroed at atmospheric pressure, the need for equalization results from a difference in the pressure measurements when both are interrogating the same site at a pressure different from 0 mmHg. Assuming the measured aortic pressure $Pa_1$ is 100 mmHg (represented by arrow 1) and the measured distal pressure $Pd_1$ is 90 mmHg (represented by arrow 2), the calculated ratio $Pd_1/Pa_1$ is 0.90. FIG. 2 shows the known method of equalizing a pressure guidewire against the aortic pressure transducer, as also disclosed in U.S. Pat. No. 6,565,514, where an offset is added to the distal pressure measurements Pd* (represented by arrow 3). More specifically, the difference $Pa_1$–$Pd_1$ (10 mmHg here) is added to every distal pressure measurement Pd' once equalized.

Equalized distal pressure measurements are therefore obtained as follows:

$$Pd^* = Pd' + (Pa_1 - Pd_1)$$

where $Pa_1$ is the aortic pressure just prior to the equalization, $Pd_1$ is the distal pressure just prior to the equalization at the site of the aortic pressure, Pd' is the measured distal pressure prior to adding the offset.

With such an equalization method, the distal pressure spans over 90 mmHg instead of 100 mmHg for the aortic pressure. The consequence is that distal pressure does not respond as much as the aortic pressure. Assuming the pressure guidewire is across a lesion causing a pressure drop equivalent to Pd/Pa equal to 0.60, this pressure drop applies to a reduced span of 90 mmHg (represented by arrow 4). While such a lesion should lead to a final Pd/Pa equal to 0.60, the equalization method causes an error that leads to a Pd/Pa equal to 0.64 (represented by arrow 5) in view of the addition of $Pa_1$–$Pd_1$, hence overestimating the Pd/Pa value, or equivalently the FFR value, as exemplified in FIG. 2.

Figure 3:
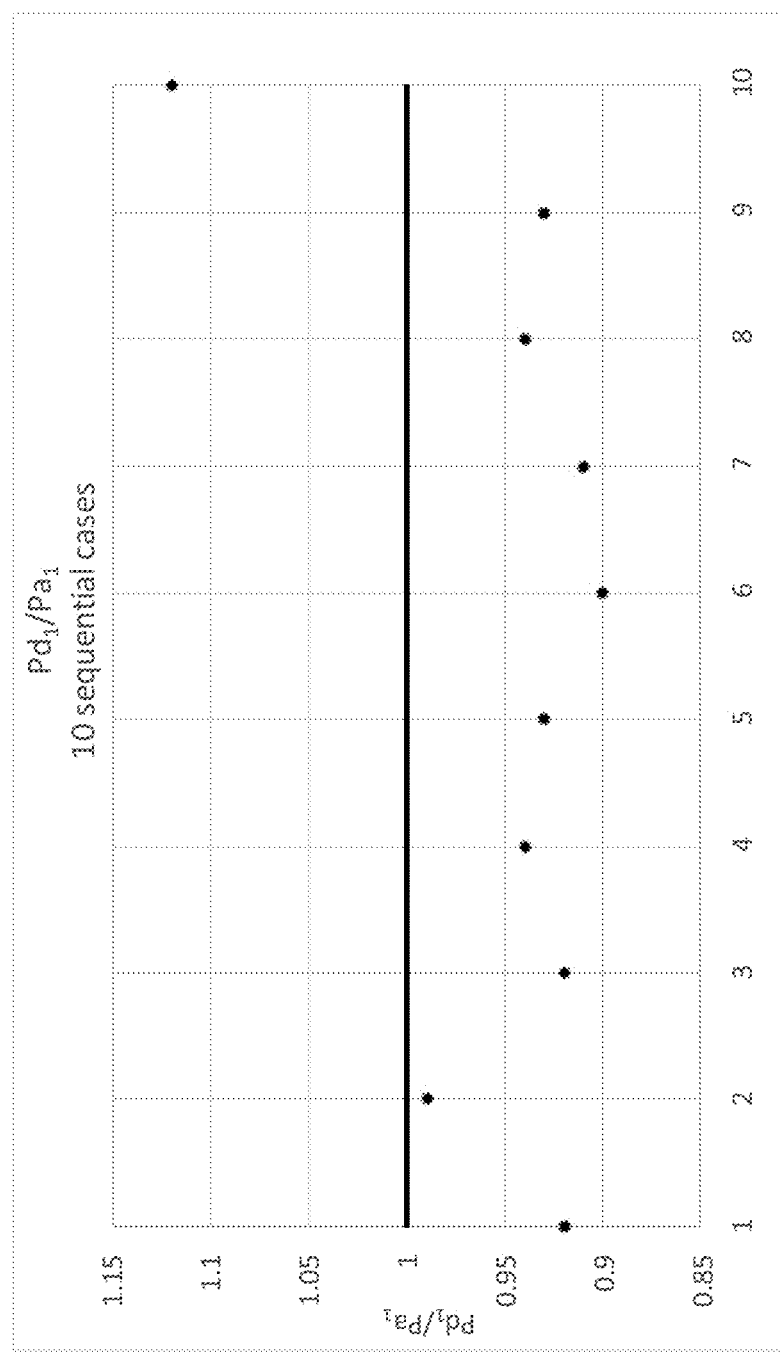
FIG. 3 is a graph which shows the gain error as measured with 10 consecutive devices currently in the market place.

FIG. 3 shows gain error from 10 consecutive devices currently on the market. The initial $Pd_1/Pa_1$, i.e., Pd/Pa before equalization, varies from 0.90 to 1.12, with most devices exhibiting an initial $Pd_1/Pa_1$ between 0.90 and 0.94.

Using the nomenclature of FIG. 1, the error that results from a pressure guidewire having a gain error but equalized by adding an offset as shown in FIG. 2 is calculated herein below.

Assuming the following definitions, $$R_1 = \frac{P_{d1}}{P_{a1}};$$

$$R_2 = \frac{P_{d2}}{P_{a2}};$$

where $Pa_1$ is the aortic pressure just prior to equalization, $Pd_1$ is the distal pressure just prior to equalization at the site of the aortic pressure, $Pa_2$ is the aortic pressure after the procedure at the time the pressure guidewire is back into the guiding catheter at the site of the aortic pressure and at the time when $Pd_2$ is simultaneously measured.

The offset added to the measured distal pressure to be equalized is given by the following relation:

$$\text{offset} = (P_{a1} - P_{d1}) = \left(1 - \frac{P_{d1}}{P_{a1}}\right) \cdot P_{a1} = (1 - R_1) \cdot P_{a1};$$

The drift post-procedure is given by the following relation:

$$\text{Drift} = (P_{a2} - P_{d2}) = \left(1 - \frac{P_{d2}}{P_{a2}}\right) \cdot P_{a2} = (1 - R_2) \cdot P_{a2};$$

The displayed minimum distal pressure $P^*_{dMin}$ as read by a pressure guidewire with a gain error equalized with the addition of an offset is given by:

$$P^*_{dMin} = \text{offset} + P^*_{aMin} \cdot R_1 \cdot \text{FFR} - \text{Drift}$$

where FFR is the true physiological FFR value.
The displayed FFR value FFR*, as read with a pressure guidewire equalized with an offset is given by:

$$FFR^* = \frac{P^*_{dMin}}{P_{aMin}} = \frac{\text{offset} + P_{aMin} \cdot R_1 \cdot FFR - \text{Drift}}{P_{aMin}}$$

The error in the reading of the true FFR value, $\Delta$FFR, i.e., the difference between the displayed FFR (FFR*) and the true FFR (FFR), is given as follows:

$$\Delta FFR = FFR^* - FFR = \frac{\text{offset} + P_{dMin} - \text{Drift}}{P_{aMin}} - FFR$$

$Pd_{Min}$ defined as the true Pd value, i.e., $P_{dMin} = P_{aMin} \cdot R_1 \cdot FFR$. By using the definition above, one can simplify the equation as follows:

$$\Delta FFR = (1 - R_1) \cdot \left(\frac{P_{a1}}{P_{aMin}} - FFR\right) - (1 - R_2) \cdot \frac{P_{a2}}{P_{aMin}}$$

Figure 4:
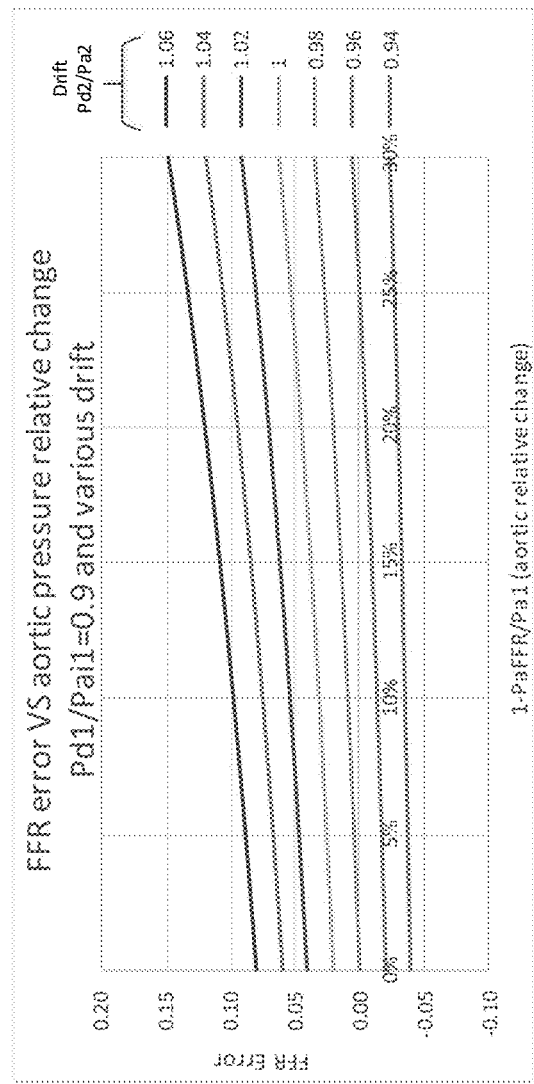
FIG. 4 is a graph which illustrates the FFR error caused by an initial $Pd_1/Pa_1$ value of 0.90 against relative change of aortic pressure $(1-Pa_{Min}/Pa_1)$. The FFR error is calculated for values of drifts ($Pd_2/Pa_2$) varying from 0.94 to 1.06.
Figure 5:
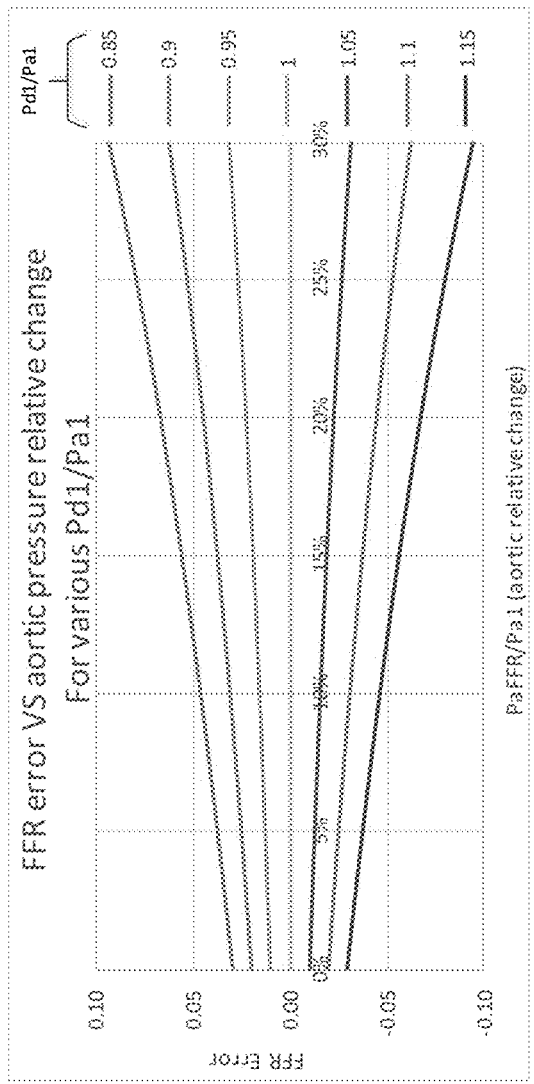
FIG. 5 is a graph which illustrates the error caused by various initial $Pd_1/Pa_1$ as function of aortic pressure change in the absence of drift.

FIG. 4 illustrates the FFR error ($\Delta$FFR) caused by an initial $Pd_1/Pa_1$ value of 0.90 against relative change of aortic pressure $(1 - Pa_{Min}/Pa_1)$. The FFR error is calculated for values of drifts $(Pd_2/Pa_2)$ varying from 0.94 to 1.06. Although the values of aortic pressure change, initial $Pd_1/Pa_1$ and drifts $Pd_2/Pa_2$ are values commonly seen in the field, the error obtained varies from −0.04 to 0.15, where clinically significant error is considered as 0.02. Similarly, FIG. 5 illustrates the error caused by various initial $Pd_1/Pa_1$ as a function of aortic pressure change in the absence of drift. FFR error is still clinically significant.

One cause that may explain the variability in the gain of the guidewire pressure sensor is the aging of sensor packaging. For example, the silicone layer protecting the sensor may harden as a result of aging, which in turn results in a reduction of sensitivity, hence a $Pd_1/Pa_1$ lower than 1.00.

Figure 6:
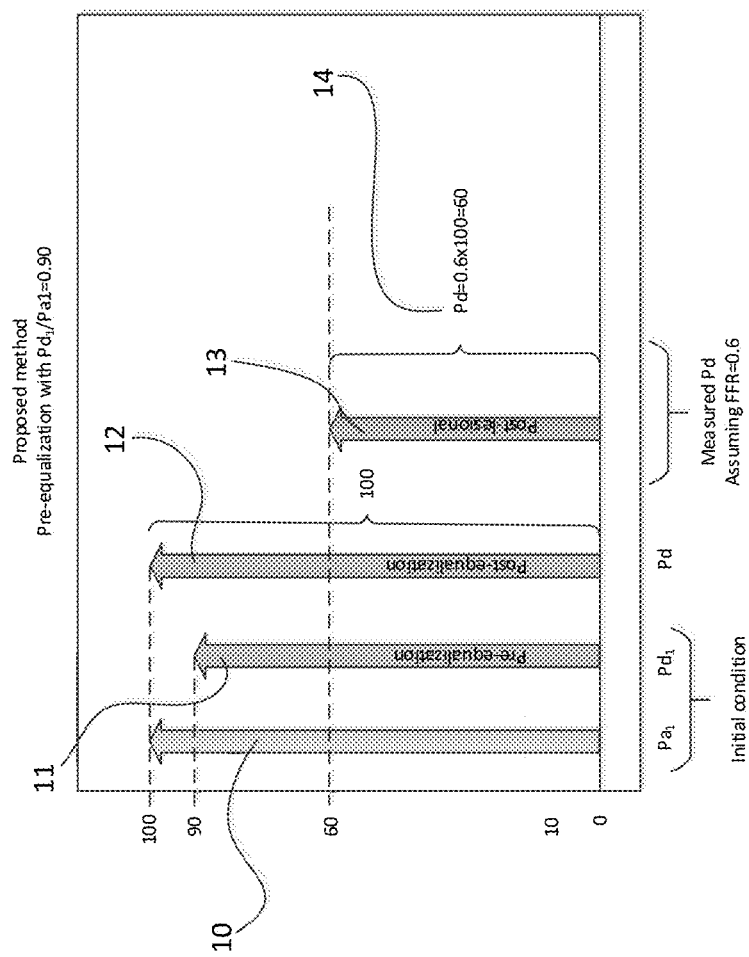
FIG. 6 is a chart which illustrates the equalization method by of gain adjustment.

An advantageous method of equalizing the distal pressure with the aortic pressure, or equivalently equalizing the aortic pressure with the distal pressure, is one where the pressure is equalized by way of adjusting the gain of one relative to the other rather than adding an offset as shown in FIG. 6. Post-equalized distal pressure Pd is in this case adjusted by multiplying each distal pressure measurement Pd' by $Pa_1/Pd_1$.

Post-equalized distal pressure measurements are obtained as follows:

$Pd = Pd' \cdot (Pa_1/Pd_1)$ (represented by arrow 12);

where $Pa_1$ is the aortic pressure just prior to the equalization (represented by arrow 10), $Pd_1$ is the distal pressure at the site of aortic pressure just prior to the equalization (represented by arrow 11), Pd' is the measured distal pressure prior to multiplying by factor $Pa_1/Pd_1$. In the example illustrated in FIG. 6, assuming an FFR of 0.6, the post-equalized distal pressure measurement (Pd) after crossing the lesion and inducing hyperemia will be 60; i.e., 0.6·100=60.

One problem with the above method of gain adjustment is that the currently available pressure guidewires, once used in the vascular system, are prone to drift, a drift where the distal pressure error is equivalent to a pressure offset. Such drifts are typically caused by a change in the resistance of one of the two resistors build within the guidewire mounted piezo-electric pressure sensor used to sense the distal pressure. If one of these resistors changes, the pressure will step up or down, but with no change to the sensitivity (or gain) of the sensor. For example, for a pressure drift of 10 mmHg, all subsequent pressure measurements will be offset by the same 10 mmHg.

Electrical pressure guidewire comprise a piezo-sensor comprising two resistors; i.e., one resistor to measure pressure and one resistor to compensate for temperature. Those two resistors are configured as a half-wheatstone bridge, and connected to a second external half-wheatstone bridge via a connector interface cable. The connector interface cable connects to three contacts on the proximal end of the pressure guidewire. Any change in the resistance of one of the four resistors within the wheatstone bridge, or any change in the contacting resistance between those parts will result in a pressure offset, without impact to the sensitivity of the sensor against pressure.

Therefore, moisture migrating within the silicone layer used to protect and isolate the piezo-electric sensor can cause the silicone to become more conductive, hence inducing a shunt resistance between the resistors that causes a pressure offset. Contact resistance between the guidewire connector and the interface cable may vary as a result of a disconnection/reconnection, hence creating a pressure offset. It is therefore evident that correcting such a drift by way of adjusting the gain would lead to erroneous FFR measurements similar to the FFR errors discussed above.

By way of non-limiting examples, Table 1 illustrates a few types of errors that may cause a pressure guidewire to deliver erroneous pressure measurements. It should be appreciated here that the potential causes of error provided in Table 1 remain design dependent, where for example a badly designed optical pressure guidewire may exhibit connection errors even if optical pressure guidewires can be designed not to cause connection errors. Similarly, assuming a sensor gain error is dependent upon the aging of the silicone layer covering the sensor, the gain error will be dependent upon the softness and stability of the silicone covering said sensor and hence, it is design dependent. The equalization strategy is therefore dependent upon the type of error as illustrated in Table 1. Gain equalization is therefore the equalization method of choice in presence of a sensor gain error and an air bubble escaping after being trapped during first insertion. It is of importance to note that those types of error are mostly susceptible to occur at the beginning of the procedure.

TABLE 1

| Types of error | Pressure GW | | Equalization |
| --- | --- | --- | --- |
| | Electrical | Optical | Strategy |
| Sensor gain error | x | x | Gain |
| First insertion trapped bubble escape | x | x | Gain |
| Height of ext. Transducer | x | x | Offset |
| Bubble appearance after insertion | x | NA | Offset |
| Moisture in silicone | x | NA | Offset |
| Connection | x | NA | Offset |

Figure 7:
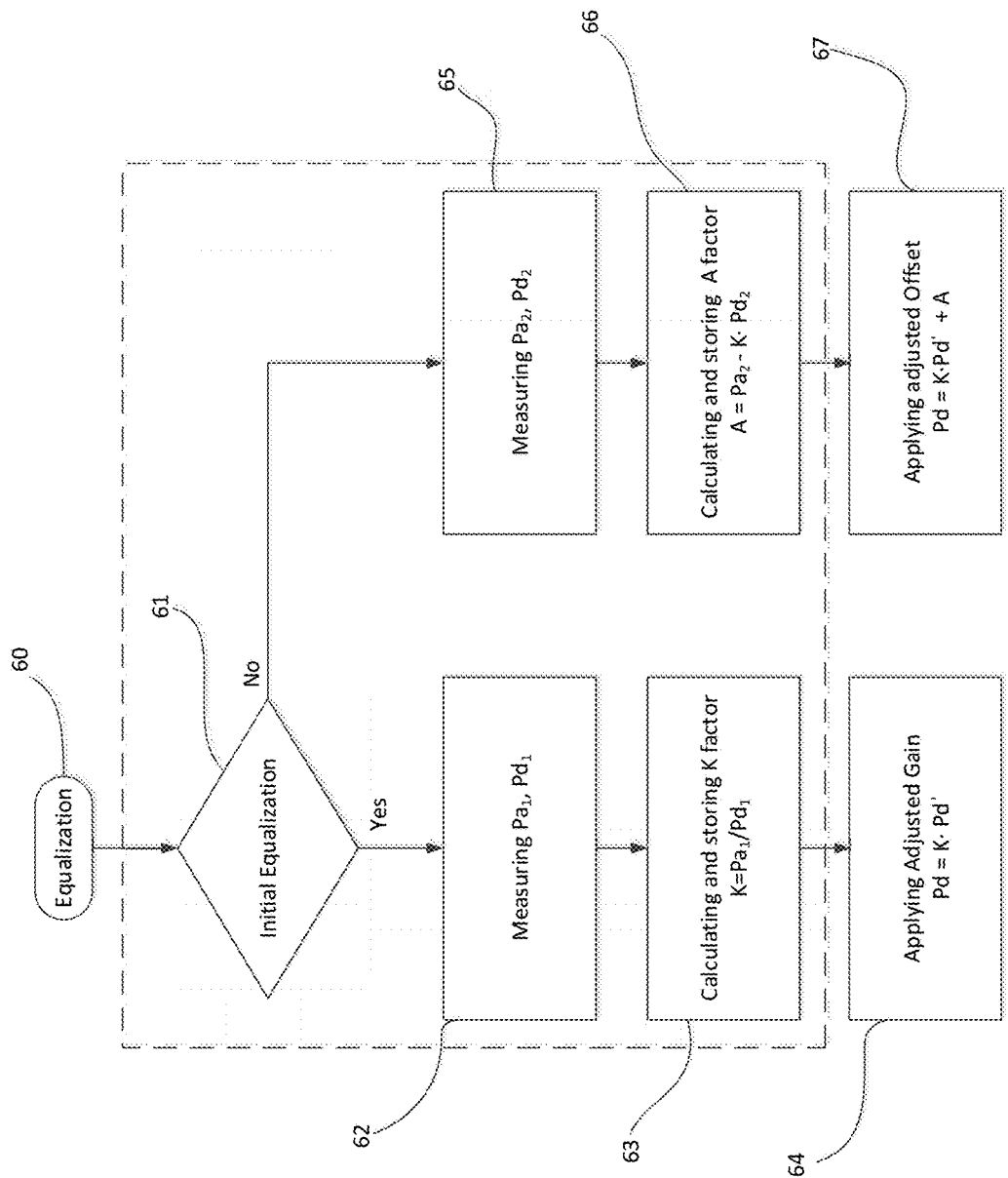
FIG. 7 is a schematic which shows a method of combining equalization methods that involve gain and offset adjustment, in accordance with an embodiment.

Another advantageous method consists in equalizing the distal pressure measurements, or equivalently the aortic pressure measurements, by applying the proper equalization method when needed. For example, at the beginning of the procedure, i.e., the first time the pressure guidewire is brought at the distal end of the guiding catheter, the risk of sensor drifting is minimal as it typically takes some time for the drift to take place. The initial equalization should therefore be performed by adjusting the gain of one sensor against the other. FIG. 7 shows such a scheme where upon equalizing, the method 60 comprises at least the following steps:

step 61:—the system detects that the equalization is performed for the first time, or similarly the system detects a situation that is recognized as equivalent to an initial equalization;

step 62:—the system measures both $Pa_1$ and $Pd_1$;

step 63:—it calculates and stores the gain factor $Pa_1/Pd_1$;

step 64:—from thereon, the system multiplies every subsequent distal pressure measurements Pd' as follows:

$$Pd=Pa_1/Pd_1 \cdot Pd' \text{(or } K \cdot Pd')$$

Upon equalizing a second time, or similarly upon equalizing in a situation that is recognized as equivalent to a second time, the method comprises the following steps:

step 61:—the system detects that the equalization was performed previously, or similarly the system detects a situation that is recognized as equivalent to a second equalization;

step 65:—the system measures both $Pa_2$ and $Pd_2$;

step 66:—it calculates and stores the offset $A=Pa_2-K \cdot Pd_2$;

step 67:—from thereon, the system offsets every subsequent distal pressure measurements Pd' as follows:

$$Pd=K \cdot Pd'+A$$

Figure 8:
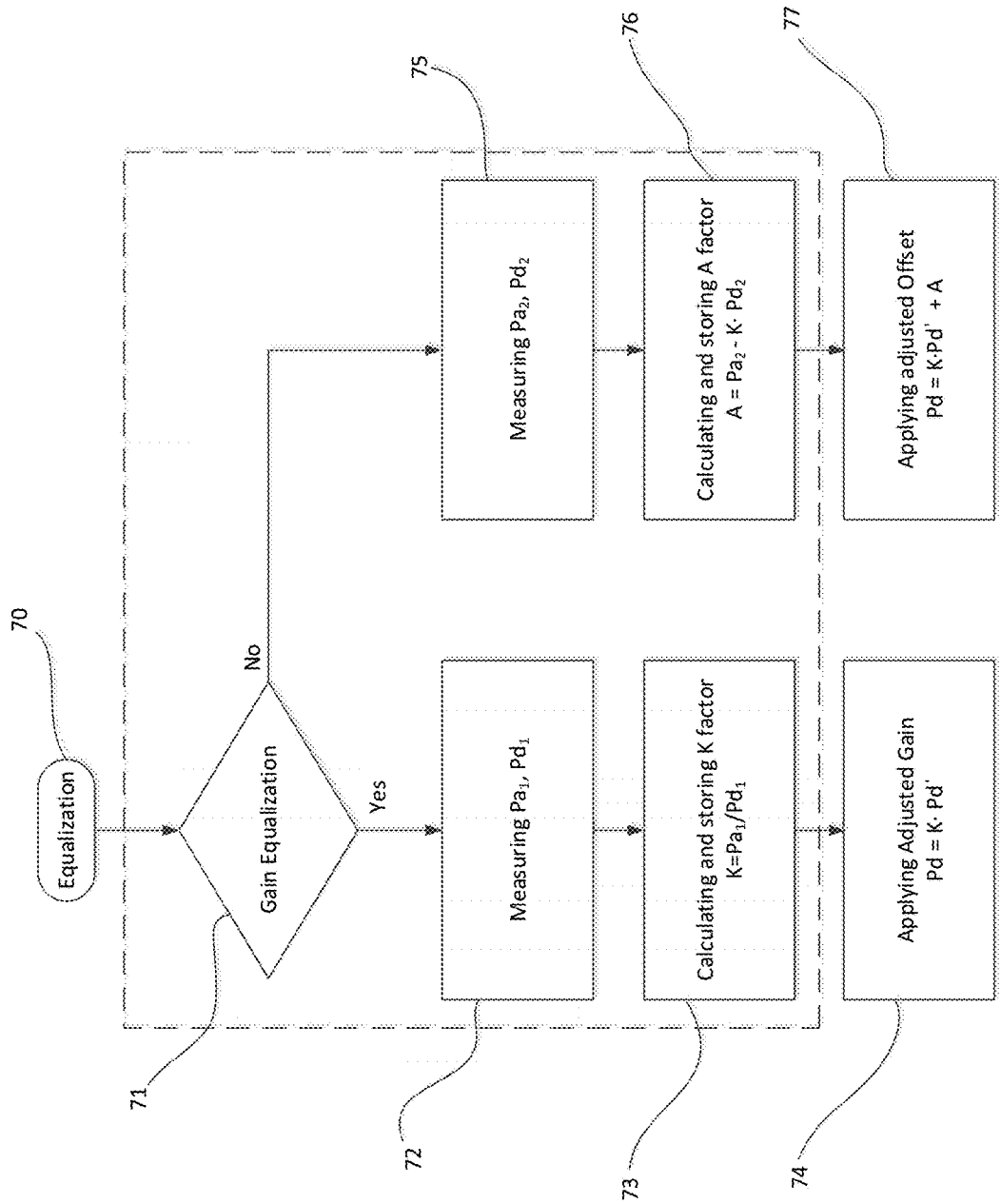
FIG. 8 is a schematic which shows a method of combining equalization methods that involve gain and offset adjustment, in accordance with an embodiment.

FIG. 7 illustrates a method that memorizes whether the equalization was performed previously or not. Another advantageous method consists in a generalization of the method for detecting whether the equalization shall be performed by adjusting the gain or adding an offset as illustrated in FIG. 8. A computerized system can comprise an algorithm that allows the recognition of the best applicable equalization method and determines whether gain equalization is required. Exemplary criteria used as input for such an algorithm include, but are not limited to, a certain time elapsed, the recording, by a monitoring device 1100, of data for a first FFR measurement, etc. Step 71 can include other factors such as the time difference between subsequent equalization attempts. For example, upon first equalization, one method would consist in waiting a given period before allowing incrementing to the so-called offset equalization method. It is indeed known by those in the art that re-equalization often reoccurs a few seconds or a few minutes after first equalization as it may be desired to improve the quality of such first equalization. Artifacts may have been present at the time of equalization and it may be desired to re-attempt equalization. According to an embodiment, the given period is between 5 seconds and 5 minutes; however, an offset equalization is usually preferred to a gain equalization after one minute is elapsed, since the events having occurred after one minute are usually those that require the offset equalization to be performed (see Table 1). According to an embodiment, the method for detecting whether the equalization shall be performed by adjusting only the gain or by adjusting the gain and adding an offset comprises verifying if actual recorded measurements were performed. Indeed, at the beginning of the procedure, sample measurements are taken to be able to apply the gain equalization described above. Right after that moment, the user of the pressure devices may feel that the gain equalization was not correct (strange results, changing conditions) and perform it again before doing any actual recorded measurements. When the user feels that the gain equalization was performed under the right circumstances, they may use that gain (factor K) for actual measurements that are recorded in order to calculate the FFR. After these recorded measurements were performed, the changing conditions that are occurring are likely to be those which require an offset equalization (see Table 1). Therefore, whether or not an actual recording was performed by the monitoring device 1100 is a good indicator of which type of equalization must be applied as a correction to the initial equalization. Therefore, a processor in the monitoring device 1100 should verify in the memory if the recording has been performed at least once in order to decide which equalization (gain or offset) needs to be applied.

FIG. 8 shows such a scheme where upon equalizing, the method 70 comprises at least the following steps:

step 71:—the system determines whether gain equalization is required (for example, if no measurements were ever performed during the current procedure, or if initial measurements were performed but no actual recording to determine FFR);

step 72:—if gain equalization is required, the system measures both $Pa_1$ and $Pd_1$;

step 73:—it calculates and stores the gain factor $Pa_1/Pd_1$;

step 74:—from thereon, the system multiplies every subsequent distal pressure measurements Pd' as follows:

$$Pd=Pa_1/Pd_1 \cdot Pd' \text{(or } K \cdot Pd')$$

Upon equalizing a second time, or similarly upon equalizing in a situation that is recognized as equivalent to a second time, the method comprises the following steps:

step 71:—the system determines whether gain equalization is required;

step 75:—if gain equalization is not required, the system measures both $Pa_2$ and $Pd_2$;

step 76:—it calculates and stores the offset value $A=Pa_2-K \cdot Pd_2$;

step 77:—from thereon, the system offsets every subsequent distal pressure measurements Pd' as follows: $Pd_{offset}=K \cdot Pd'+A$, where $Pd_{offset}$ is the gain- and offset-equalized value of the distal pressure.

It should be noted that equivalents of the above calculations can be performed. For example, it would be possible to define another constant K' as the ratio of $Pd_1/Pa_1$. One would then have $Pd=Pd'/K'=K \cdot Pd'$.

Equalization (including gain-equalization and possibly offset-equalization) can also be performed on the aortic pressure. Measured aortic pressures Pa' can be corrected (equalized) by dividing Pa' by K (or multiplying Pa' by K'=1/K), thereby calculating Pa, which is gain-equalized. If necessary, the offset value can be calculated: A'=Pd$_2$−K·Pa$_2$. This offset can then be used for an offset equalization (under given circumstances detailed above) after the gain-equalization, as follows: Pa$_{offset}$=K'·Pa'+A', where Pa$_{offset}$ is the gain- and offset-equalized value of the aortic pressure.

Afterwards, the FFR can be calculated. The FFR is the minimum value of the ratio Pd/Pa, where the gain equalization and possibly an offset equalization were performed to have more accurate values of the Pd, hence of Pd/Pa ratio. Preferably, the FFR is the minimum value of the ratio [Pd]/[Pa], where the brackets [ ] represent an average value which aims at removing the pressure variations due only to the cardiac cycle, the ups and downs occurring at each heartbeat being irrelevant to the FFR determination. The average value is usually a multi-cardiac-cycle moving average of the measured pressures. Averaging on three cardiac cycles is typical. Other types of averaging, such as a single-cardiac-cycle moving average, or non-moving averages, are also possible. It should be noted that mentions of Pd and Pa in the present description usually refers to their averaged value. The averaging can also be performed on the equalized pressure values.

The method of FIG. 8 also includes the contribution of the operator, where a skilled operator may be given the choice of equalizing by way of either adjusting the gain or adding an offset. This can be implemented by an interface giving the operator such a choice of equalization. For example, the presence of an air bubble present on the surface of the sensor at the time of equalization would lead to an undesirable additional pressure that is inversely proportional to the size of the air bubble. Upon waiting a certain time, the air bubble may escape, in which case the measured pressure will drop without a change in the zero value of the pressure sensor. In such a circumstance, the equalization should be performed again by re-equalizing by way of adjusting the gain.

More newly developed optical pressure guidewires, although less prone to drift caused by disconnection/reconnection, exhibit some of the same problems related to equalization and therefore, the present disclosure applies equally to electrical, optical or other guidewire or catheter mounted pressure devices.

Figure 9:
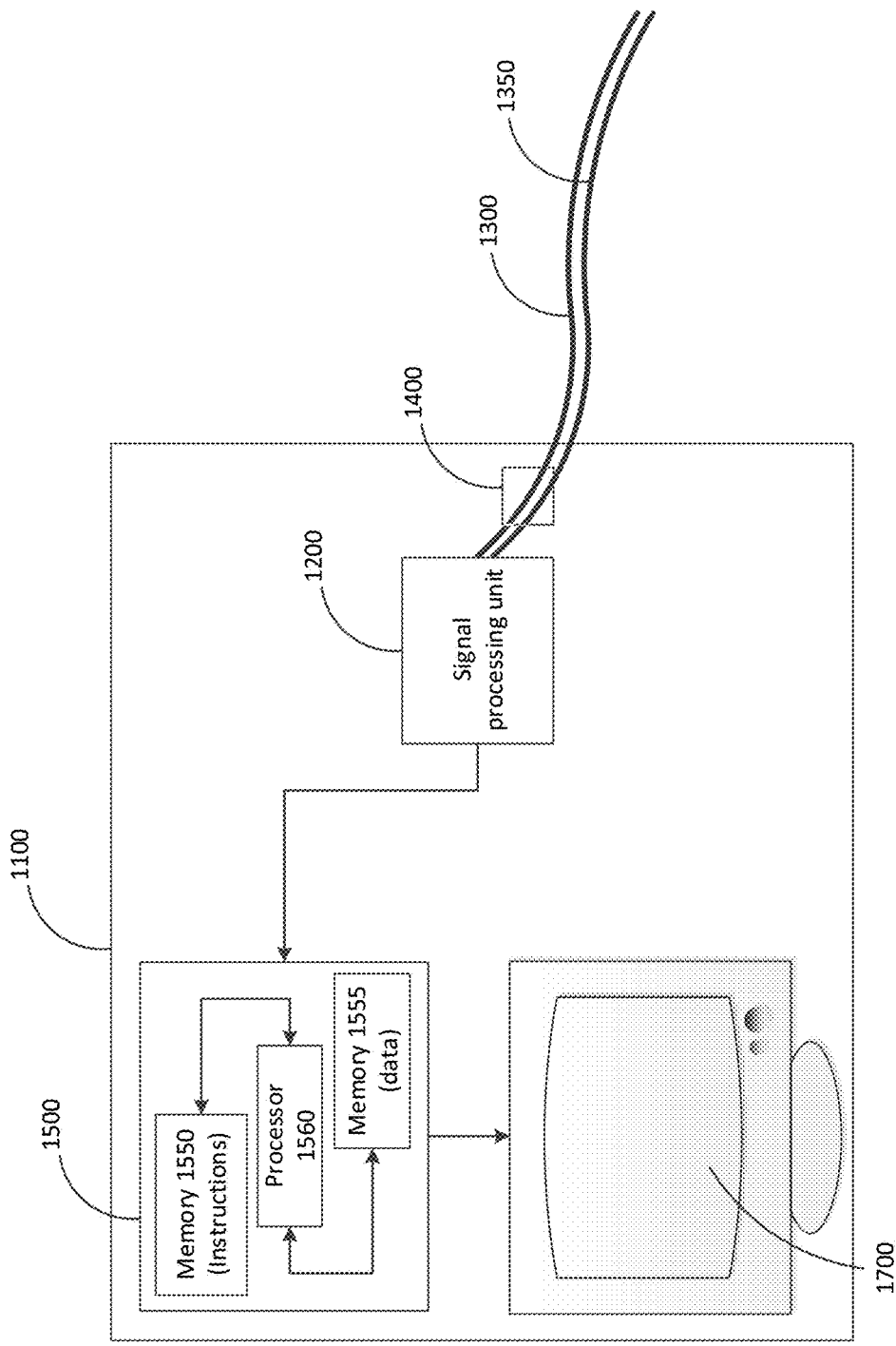
FIG. 9 is a schematic which shows a system for combining equalization methods that involve gain and offset adjustment, according to an embodiment.

Various ways of implementing the equalization method described above may be contemplated. However, all of these embodiments of a system used in performing of fractional flow reserve (FFR) measurements in which takes place an equalizing of a distal pressure against an aortic pressure involve some equipment, as shown in FIG. 9. Indeed, the system comprises a distal intravascular pressure device 1300 for measuring distal pressure and an aortic pressure device 1350 for measuring aortic pressure. The system further comprises a monitoring device 1100 for performing the monitoring. The monitoring device 1100 comprises an input for receiving signals from the pressure devices. For example, the pressure devices (1300, 1350) can be electrically connected to the monitoring device. If an optical intravascular pressure device is used, the connection will be an optical connection, and may additionally involve an optical-to-electrical signal converter. In this case, the monitoring device 1100 may also act as a signal conditioner unit, i.e., the optical input may also serve as an optical output for sending the signal into the optical fiber of the intravascular pressure device (pressure is measured by analyzing the returned signal inputted into the monitoring device 1100). Regardless of the technology being used, the pressure is usually determined by analyzing a signal carried by the intravascular pressure device to the monitoring device. The monitoring device 1100 therefore comprises a signal processing unit 1200 for detecting and processing the signal into a useful value (pressure) or series of values (digital representation of the received signal, such as a time series or frequency spectrum) for use by a computer 1500. The pressure value, which is calculated by either the signal processing unit 1400 or the computer 1500, is usually implicitly carried by the physical state of the signal (e.g., modulation of the signal, phase shift of a reflected signal, shape of the received signal, etc.). The signal input 1400 is the link between the intravascular pressure device 1300 and the signal processing unit 1200. The signal processing unit 1200 comprises a suitable detector and is thus connected to the signal input 1400 of the monitoring device 1100.

The monitoring device 1100 comprises the computer 1500 in communication with the signal processing unit 1200 and receiving a digital representation of the signal (or pressure values pre-calculated by the signal processing unit 1200) therefrom. The term "computer" is meant to include computing devices in a broad manner. For instance, a computer can comprise a complete computer (various components assembled inside an enclosure) with peripherals (screen, keyboard, mouse, etc.), or only minimal electronic components (electronic chips, microcontrollers, etc.) assembled to make computations and take decisions. A remote computer (with the required network to communicate data), a mobile computer, a server, or other types of computing machines may be contemplated too. Usually, the computer is the electronic portion inside the enclosure that makes up the monitoring device 1100.

The computer 1500 comprises a memory 1550 for storing instructions thereon, and a memory 1555 for storing inputted data and outputted data (corrected pressure measurements, FFR) thereon (they may be the same memory or be distinct ones). The instructions stored on the memory 1550 are meant to make the computer 1500 perform the calculations and decisions required in the method described above. Such calculations and decisions are performed by a piece of hardware (e.g., an electronic chip), usually called a processor 1560 (or other derivatives of that term, such as a CPU, a processing device, and the like). Since the purpose of the method described above comprises providing a more accurate measure of the FFR than in prior methods during a medical or surgical intervention (in which time matters and decisions need to be taken fast), the computer 1500, with its ability to give accurate results in a timely manner, is essential for practicing the method. When the computer 1500 receives input from the intravascular pressure device(s) 1000, it may apply the necessary operations on the values implicitly contained in the signal to provide the professional with accurate FFR measures. This contrasts with the inaccurate FFRs given by prior art methods which failed to apply gain corrections to the signals received from the intravascular pressure devices, those signals carrying sometimes inadequate values due to the use of the intravascular pressure device(s) (bubbles, contact losses at interfaces and the like). The technical problem of inaccurate values carried by the signals provided by the pressure devices (1300, 1350) because of physical changes occurring on this equipment is thus solved by applying relevant corrections by the computing machine 1500 which processes the values carried by the signal. This process thus mitigates the error in such values caused by the imperfections of the equipment being used (i.e., lack of reliability/repeatability of measurements, see causes in Table 1).

The monitoring device 1100 advantageously comprises a display 1700 that is adapted to display the FFR measurement to the professional using the system. According to an embodiment, the display 1700 is further adapted to display real-time values of the measured pressures (either before or after corrections are applied thereto). The display 1700 is thus operably connected to the computer 1500.

The present invention is not limited to the above described preferred embodiments and methods. Various alternatives, modifications and equivalents may be used in the ways the offset and gain equalization methods are implemented. Therefore, the above embodiments should not be taken as limiting the scope of the invention, which is defined by the appended claims.

The invention claimed is:

1. A method for equalizing one of a pressure of a distal intravascular pressure measuring device (a distal pressure) and a pressure of an aortic pressure measuring device (an aortic pressure), the method comprising:
measuring an initial aortic pressure ($Pa_1$) at a site of aortic pressure using a guidewire comprising the aortic pressure measuring device and measuring an initial distal pressure ($Pd_1$) at the site of aortic pressure using the guidewire comprising the distal intravascular pressure measuring device, the guidewire comprising an optical connection to transmit a signal to undergo equalization;
calculating a gain factor (K) by dividing the initial aortic pressure ($Pa_1$) by the initial distal pressure ($Pd_1$);
measuring the aortic pressure (Pa') and the distal pressure (Pd') at a site that is distal to the site of the aortic pressure; and
repeatedly equalizing the pressure by performing one of:
if gain-equalizing was not previously performed, gain-equalizing by adjusting a gain of one of:
the measured distal pressure by multiplying Pd' by the gain factor (K), thereby producing a gain-equalized distal pressure ($Pd_{eq}$); and
the measured aortic pressure by dividing Pa' by the gain factor (K), thereby producing a gain-equalized aortic pressure ($Pa_{eq}$); and
if the gain-equalizing was previously performed, adding an offset value (A) to the pressure.

2. The method of claim 1, wherein gain-equalizing comprises gain-equalizing the measured distal pressure, further comprising averaging the distal pressure, either before or after the gain-equalizing, thereby generating an average gain-equalized distal pressure ([Pd]); averaging the aortic pressure, thereby generating an average aortic pressure ([Pa]); and calculating fractional flow reserve (FFR) by calculating the minimum value of ratio [Pd]/[Pa].

3. The method of claim 2, wherein the averaging is performed over one of:
a given number of cardiac cycles; and
a given time period.

4. The method of claim 1, wherein adding the offset value to the pressure comprises performing an offset equalization of the gain-equalized distal pressure, comprising:
verifying that the gain factor (K) has been used for the gain-equalizing to determine if gain-equalizing was not previously performed;
measuring an aortic pressure ($Pa_2$) using the aortic pressure measuring device and measuring a distal pressure ($Pd_2$) at the site of aortic pressure using the distal intravascular pressure measuring device;
calculating the offset value (A) by subtracting the gain-equalized distal pressure from the aortic pressure ($Pa_2$); and
offset-equalizing by calculating a gain-and offset-equalized distal pressure ($Pd_{offset}$) by adding the offset value (A) to the gain-equalized distal pressure ($Pd_{eq}$).

5. The method of claim 4, further comprising averaging the distal pressure, either before or after the gain-equalizing, thereby generating an average gain-equalized distal pressure ([Pd]); averaging the aortic pressure, thereby generating an average aortic pressure ([Pa]); and calculating fractional flow reserve (FFR) by calculating the minimum value of ratio [Pd]/[Pa].

6. The method of claim 4, further comprising determining whether the offset-equalizing is required, the determining comprising: verifying at least one of a set of criteria, the set of criteria comprising: an existence of a bubble on a surface of the distal intravascular pressure measuring device; a manipulation of the distal intravascular pressure measuring device during more than 2 minutes; and a recording of data for a first FFR measurement.

7. The method of claim 5, wherein verifying that the distal pressure is gain-equalized comprises verifying that a recording has been performed at least once by a monitoring device.

8. The method of claim 1, further comprising determining whether another gain-equalizing is required after performing a first gain-equalizing.

9. The method of claim 8, wherein the determining whether another gain-equalizing is required comprises determining whether a second equalizing step is required, measuring a period after the first gain-equalizing and, upon determining that a second equalizing step is required and that the period is less than a given period, performing once more the calculating a gain factor (K), the measuring a distal pressure (Pd') and the gain-equalizing the measured distal pressure (Pd').

10. The method of claim 9, wherein the given period is between 5 seconds and 2 minutes.

11. The method of claim 1, wherein the measuring a distal pressure (Pd') at a site that is distal to the site of aortic pressure comprises measuring a distal pressure (Pd') at a site that is distal to an intravascular lesion using the distal intravascular pressure measuring device.

12. The method of claim 1, wherein gain-equalizing comprises gain-equalizing the measured aortic pressure, further comprising averaging the aortic pressure, either before or after the gain-equalizing, thereby generating an average gain-equalized aortic pressure ([Pa]); averaging the distal pressure, thereby generating an average distal pressure ([Pd]); and calculating fractional flow reserve (FFR) by calculating the minimum value of ratio [Pd]/[Pa].

13. The method of claim 1, wherein adding the offset value to the pressure comprises performing an offset equalization of the gain-equalized aortic pressure, comprising:
verifying that the gain factor (K) has been used for the gain-equalizing;
measuring an aortic pressure ($Pa_2$) using the aortic pressure measuring device and measuring a distal pressure ($Pd_2$) at the site of aortic pressure using the distal intravascular pressure measuring device;
calculating the offset value (A') by subtracting the gain-equalized aortic pressure from the distal pressure ($Pd_2$); and
offset-equalizing by calculating a gain-and offset-equalized aortic pressure ($Pa_{offset}$) by adding the offset value (A') to the gain-equalized aortic pressure ($Pa_{eq}$).

14. The method of claim 13, further comprising averaging the aortic pressure, either before or after the gain-equalizing, thereby generating an average gain-equalized aortic pressure ([Pa]); averaging the distal pressure, thereby generating an average distal pressure ([Pd]); and calculating fractional flow reserve (FFR) by calculating the minimum value of ratio [Pd]/[Pa].

15. A method for equalizing a pressure of one of a distal intravascular pressure measuring device and an aortic pressure measuring device against another one thereof, the method comprising:
performing a measurement with a guidewire comprising the distal intravascular pressure measuring device and the aortic pressure measuring device, the guidewire comprising an optical connection or an electric connection to transmit a signal from the distal intravascular pressure measuring device or from the aortic pressure measuring device, the signal to undergo equalization;
repeatedly determining if gain-equalizing the pressure was previously performed; and
based on the determining, repeatedly equalizing the pressure by performing one of:
adjusting a gain of the pressure, if the gain-equalizing was not previously performed; and
adding an offset to the pressure, if the gain-equalizing was previously performed.

16. A system used in performing of fractional flow reserve (FFR) measurements in which takes place an equalizing of a distal pressure against an aortic pressure, the system comprising:
a guidewire comprising an optical connection for transmitting a signal to undergo equalization, the guidewire comprising:
a distal intravascular pressure measuring device for measuring distal pressure; and
an aortic pressure measuring device for measuring aortic pressure;
a monitoring device comprising a computer adapted to execute instructions comprising:
measuring an initial aortic pressure ($Pa_1$) at a site of aortic pressure using the aortic pressure measuring device and measuring an initial distal pressure ($Pd_1$) at the site of aortic pressure using the distal intravascular pressure measuring device;
calculating a gain factor (K) based on the initial aortic pressure ($Pa_1$) and the initial distal pressure ($Pd_1$);
measuring a distal pressure (Pd') at a site that is distal to the site of aortic pressure; and
repeatedly equalizing the pressure by performing one of:
if gain-equalizing was not previously performed, gain-equalizing the measured distal pressure by multiplying Pd' by the gain factor (K) thereby producing an equalized distal pressure ($Pd_{eq}$) and
if the gain-equalizing was previously performed, adding an offset value (A) to the pressure.

17. The system of claim 16, wherein the computer further executes instructions comprising: averaging the distal pressure, either before or after the gain-equalizing, thereby generating an average gain-equalized distal pressure ([Pd]); averaging the aortic pressure, thereby generating an average aortic pressure ([Pa]); and calculating fractional flow reserve (FFR) by calculating the minimum value of ratio [Pd]/[Pa].

18. The system of claim 16, wherein the computer further executes instructions comprising:
after the gain-equalizing, measuring an aortic pressure ($Pa_2$) using the aortic pressure measuring device and measuring a post procedure distal pressure ($Pd_2$) at the site of aortic pressure using the distal intravascular pressure measuring device;
calculating the offset value (A) by subtracting a gain-equalized distal pressure from the aortic pressure ($Pa_2$); and
calculating a gain-and offset-equalized distal pressure ($Pd_{offset}$) by adding the offset value (A) to the gain-equalized distal pressure ($Pd_{eq}$).

19. The system of claim 16 wherein the distal intravascular pressure measuring device comprises a pressure guidewire.

20. The system of claim 19, wherein the aortic pressure measuring device comprises a catheter for sliding onto the pressure guidewire.

* * * * *